(12) United States Patent
Kaneko (10) Patent No.: US 11,307,211 B2
(45) Date of Patent: Apr. 19, 2022

(54) PCR TUBE, RFID SAMPLE MANAGEMENT SYSTEM, AND RFID SAMPLE MANAGEMENT METHOD

(71) Applicant: FUJIFILM Corporation, Tokyo (JP)

(72) Inventor: Yasuhisa Kaneko, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 351 days.

(21) Appl. No.: 16/297,739

(22) Filed: Mar. 11, 2019

(65) Prior Publication Data

US 2019/0204348 A1 Jul. 4, 2019

Related U.S. Application Data

(63) Continuation of application No. PCT/JP2017/031416, filed on Aug. 31, 2017.

(30) Foreign Application Priority Data

Sep. 13, 2016 (JP) .............................. JP2016-178806

(51) Int. Cl.
*G01N 35/00* (2006.01)
*C12M 1/00* (2006.01)
(Continued)

(52) U.S. Cl.
CPC ...... *G01N 35/00732* (2013.01); *B01L 3/5453* (2013.01); *B01L 3/5457* (2013.01); *C12M 1/00* (2013.01); *G01N 35/026* (2013.01); *G06K 7/10366* (2013.01); *G06K 19/07758* (2013.01); *G06K 19/07773* (2013.01); *B01L 2300/021* (2013.01); *B01L 2300/04* (2013.01);
(Continued)

(58) Field of Classification Search
CPC ................................................. G01N 35/00732
USPC ........................................................ 435/6.12
See application file for complete search history.

(56) References Cited

U.S. PATENT DOCUMENTS

2005/0205673 A1* 9/2005 Morris ............... G06K 7/10366
235/385
2006/0283945 A1 12/2006 Excoffier et al.
(Continued)

FOREIGN PATENT DOCUMENTS

EP 2876432 5/2015
JP H02251768 10/1990
(Continued)

OTHER PUBLICATIONS

IP.com.*
(Continued)

*Primary Examiner* — Allyson N Trail
(74) *Attorney, Agent, or Firm* — JCIPRNET (57) ABSTRACT

Provided are a PCR tube that can reliably perform management of a sample, and an RFID sample management system and an RFID sample management method using the PCR tube. The PCR tube 40 includes a tube body 42 that has an opening at one end and has a collar part 46 around the opening, and a lid part 44 that is attachably and detachably mounted on the tube body 42 and seals the opening of the tube body 42 at the time of the mounting. An RFID tag 48 having a passive antenna built therein is provided at the collar part 46 or the lid part 44, and the antenna has directivity in a direction opposite to a bottom face 42a of the tube body 42.

17 Claims, 8 Drawing Sheets

(51) Int. Cl.
  *G01N 35/02* (2006.01)
  *B01L 3/00* (2006.01)
  *G06K 7/10* (2006.01)
  *G06K 19/077* (2006.01)
  *G01N 35/04* (2006.01)

(52) U.S. Cl.
  CPC ............ *B01L 2300/0832* (2013.01); *G01N 2035/00782* (2013.01); *G01N 2035/0418* (2013.01)

(56) References Cited

U.S. PATENT DOCUMENTS

| | | | |
|---|---|---|---|
| 2009/0026907 A1* | 1/2009 | Davidowitz | G01N 35/00722 312/407 |
| 2011/0263461 A1* | 10/2011 | Kastury | B01L 9/523 506/23 |
| 2012/0068085 A1* | 3/2012 | Cucin | A61B 10/0275 250/492.1 |
| 2012/0128534 A1 | 5/2012 | Minemura et al. | |
| 2013/0082099 A1* | 4/2013 | Furrer | G01N 1/28 235/375 |
| 2016/0038943 A1 | 2/2016 | Hagiwara et al. | |
| 2018/0045621 A1* | 2/2018 | Radjy | G08B 21/182 |

FOREIGN PATENT DOCUMENTS

| | | |
|---|---|---|
| JP | 2002082120 | 3/2002 |
| JP | 2005339507 | 12/2005 |
| JP | 2008197842 | 8/2008 |
| JP | 2009025144 | 2/2009 |
| JP | 2009080014 | 4/2009 |
| JP | 2011027658 | 2/2011 |
| JP | 2011196820 | 10/2011 |
| JP | 2016515805 | 6/2016 |
| WO | 2008003693 | 1/2008 |
| WO | 2009104362 | 8/2009 |
| WO | 2012145450 | 10/2012 |
| WO | 2014143044 | 9/2014 |
| WO | 2014163190 | 10/2014 |

OTHER PUBLICATIONS

"Office Action of Japan Counterpart Application", dated Mar. 2, 2020, with English translation thereof, pp. 1-8.

"Office Action of Europe Counterpart Application", dated Sep. 18, 2020, p. 1-p. 10.

"International Search Report (Form PCT/ISA/210) of PCT/JP2017/031416," dated Nov. 28, 2017, with English translation thereof, pp. 1-5.

"Written Opinion of the International Searching Authority (Form PCT/ISA/237) of PCT/JP2017/031416," dated Nov. 28, 2017, with English translation thereof, pp. 1-12.

"Search Report of Europe Counterpart Application", dated Aug. 13, 2019, pp. 1-10.

* cited by examiner

PCR TUBE, RFID SAMPLE MANAGEMENT SYSTEM, AND RFID SAMPLE MANAGEMENT METHOD

CROSS-REFERENCE TO RELATED APPLICATIONS

The present application is a Continuation of PCT International Application No. PCT/JP2017/031416 filed on Aug. 31, 2017 claiming priority under 35 U.S.C § 119(a) to Japanese Patent Application No. 2016-178806 filed on Sep. 13, 2016. Each of the above applications is hereby expressly incorporated by reference, in their entirety, into the present application.

BACKGROUND OF THE INVENTION

1. Field of the Invention

The present invention relates to a PCR tube, an RFID sample management system, and an RFID sample management method, and particularly, to a PCR tube having an RFID, and an RFID sample management system and an RFID sample management method using this PCR tube.

2. Description of the Related Art

As methods of acquiring a target cell from a plurality of cells, for example, fractionating the target cell is performed by flow cytometry. The flow cytometry is a method of dispersing cells in a fluid, allowing the fluid to flow finely, optically analyzing the cells, and performing determination and preparative isolation of a cell to be acquired on the basis of this analysis result. The fractionated cell is then analyzed. For example, in a prenatal test, the percentage of target cells during preparative isolation using the flow cytometry is about 70 percent to about 80 percent. For that reason, it is inefficient to perform analysis or pretreatment for analysis to all cells fractionated by the flow cytometry. For example, in a case where a tube is moved in order to take out the tube to be analyzed or processing and analysis are simultaneously performed in order to efficiently analyze a plurality of samples, sample management is essential so that samples are not confused.

As a method of managing samples, a method using a radio frequency identification (RFID) tag is performed. In this method, by disposing a member having an attachable and detachable RFID tag under the tube, information management of a cell within a polymerase chain reaction (PCR) tube is performed. Additionally, in the following JP2002-082120A, a living organism/biological sample container in which an integrated circuit (IC) chip is buried within the container is described.

SUMMARY OF THE INVENTION

In the prenatal diagnosis, containers for analyzing cells need only to be capable of containing one cell and are small containers. Therefore, it is difficult to describe a lot of information in each container. Additionally, in a case where the RFID tag is installed, the size of the related-art containers is large. Additionally, in the PCR tube or the like, in a case where the PCR processing is performed, a temperature is applied. Therefore, a place where the RFID tag is installed is limited.

The invention has been made in view of such circumstances, and an object thereof is to provide a PCR tube that can reliably perform sample management within the PCR tube, an RFID sample management system, and an RFID sample management method.

In order to achieve the above object, a PCR tube related to the invention comprises a tube body that has an opening at one end and has a collar part around the opening; and a lid part that is attachably and detachably mounted on the tube body and seals the opening of the tube body at the time of mounting. An RFID tag having a passive antenna built therein is provided at the collar part or the lid part. The antenna has directivity in a direction opposite to a bottom face of the tube body.

According to the PCR tube of the invention, the RFID tag is provided at the collar part of the tube body, or the lid part. Accordingly, even in a case where PCR processing is performed using the PCR tube, a temperature can be prevented from being applied to the RFID tag, and management of the information stored in the RFID tag can be reliably performed. Additionally, by making the antenna of the RFID tag have the directivity in the direction opposite to the bottom face of the tube body, the reader/writer is installed on side opposite to the bottom face of the tube body in a case where the information of the RFID tag is read by the reader/writer. Accordingly, a distance from the RFID tag can be shortened and the information of the RFID tag can be read. Hence, even in a case where the antenna is short and the range of the directivity is narrow, the reading can be made by the reader/writer. Thus, the RFID tag can be made small and the installation of the RFID tag to the collar part or the lid part is possible.

In addition, "the bottom face of the tube body" indicates a face that is in contact with the cell in a case where cell observation and the PCR processing are performed within the PCR tube.

In one aspect of the PCR tube related to the invention, it is preferable that the PCR tube further comprises a positioning part that determines a position of the RFID tag in a case where the tube body is disposed on a well plate.

According to this aspect, the positioning part in a case where the tube body is disposed in the well plate is provided. Accordingly, the positions of the RFID tags of a plurality of the PCR tubes disposed in the well plate can be the same position. Hence, the information can be reliably read without erroneously reading the RFID tag of the next PCR tube in a case where the reading is made by the reader/writer.

In one aspect of the PCR tube related to the invention, it is preferable that the positioning part is a notch part provided in the collar part.

According to this aspect, the notch part provided in the collar part is used as the positioning part. For example, alignment of the PCR tube can be easily performed by providing a protrusion on the well plate and combining the protrusion with the notch part.

In one aspect of the PCR tube related to the invention, it is preferable that the RFID tag provided at the lid part is attachable and detachable.

According to this aspect, the RFID tag provided at the lid part is made attachable and detachable. Accordingly, the RFID tag can be reused and costs can be reduced.

In one aspect of the PCR tube related to the invention, it is preferable that the RFID tag is disposed within a structural body made of a light-transmissive material, and the lid part has a recess to which the structural body is attachable in a fitting manner.

According to this aspect, the recess into which the structural body having the RFID tag at the lid part can be fitted is provided. Accordingly, exchange of the structural body can be easily performed. Additionally, by forming the structural body from the light-transmissive material, the sample within the PCR tube can be imaged.

In one aspect of the PCR tube related to the invention, it is preferable that the light-transmissive material is a material selected from polypropylene, polystyrene, and acrylic resin.

This aspect describes specific examples of the light-transmissive material, and the sample within the PCR tube can be imaged by using the above materials.

In one aspect of the PCR tube related to the invention, it is preferable that a code configured in one dimension or two dimensions is described in the tube body.

According to this aspect, the code configured in one dimension or two dimensions is described in the tube body. Accordingly, the information can be individually read by a code reader. Additionally, in a case where the information cannot be read due to a failure of the RFID tag, the information is read from the code configured in one dimension or two dimensions. Accordingly, the sample can be managed.

In one aspect of the PCR tube related to the invention, it is preferable that at least any one of information of the cell or arrangement information of the tube body on the well plate is described in the tube body.

According to this aspect, the information of the cell or the arrangement information of the tube body on the well plate is described. Accordingly, the sample within the PCR tube can be visually checked, without performing the reading with a reader.

In order to achieve the above object, an RFID sample management system of the invention comprises the PCR tube described above; a well plate having a well holder in which the PCR tube is disposed; and an RFID reader/writer that has a reader/writer antenna and is capable of being disposed on a side opposite to the bottom face of the tube body.

According to the RFID sample management system of the invention, the PCR tube described above is used. Accordingly, the directivity of the antenna of the RFID tag provided in the PCR tube is the side opposite to the bottom face of the tube body. By making it possible to dispose the RFID reader/writer on the side opposite to the bottom face of the tube body, the information of the sample within the PCR tube can be reliably read from the RFID tag, and the sample can be managed by the RFID tag.

In one aspect of the RFID sample management system related to the invention, it is preferable that a plurality of the reader/writer antennas are provided and the plurality of reader/writer antennas are disposed at positions corresponding to the well holders of the well plate.

According to this aspect, the reader/writer antennas provided in the reader/writer are respectively disposed at the positions corresponding to the well holders of the well plate. Accordingly, the information of the plurality of RFID tags can be read at a time.

In one aspect of the RFID sample management system related to the invention, it is preferable that the system further comprises scanning means for scanning the RFID reader/writer.

According to this aspect, the scanning means for scanning the RFID reader/writer is provided to scan the RFID reader/writer. Accordingly, the information of the RFID tags of the plurality of PCR tubes can be read. Additionally, in a case where the read information is made by the RFID reader/writer, the read information is information of a PCR tube under the RFID reader/writer. Therefore, the read information and the sample within the PCR tube can be reliably made to correspond to each other and can be prevented from being erroneously recognized.

In one aspect of the RFID sample management system related to the invention, it is preferable that the system further comprises determination means for determining whether or not next processing of a cell within the tube body is to be performed; and display means for displaying the cell determined to be subjected to the next processing by the determination means.

According to this aspect, the display means for displaying a cell determined to be subjected to processing next to the cell within the tube body is provided. Accordingly, even in a case where the RFID reader/writer is moved from a state where the RFID tag is read, a PCR tube containing a cell on which the next processing is performed can be checked.

In one aspect of the RFID sample management system related to the invention, it is preferable that the display means is provided on the bottom face side of the tube body.

According to this aspect, the display means is provided on the bottom face side of the tube body. Accordingly, the PCR tube having the cell on which processing is performed can be visually and easily checked. The PCR reader/writer is disposed on the side opposite to the bottom face of the tube body in a case where the information is read from the RFID tag. Hence, in a case where the PCR tube is taken out from the well plate, the PCR reader/writer should be moved. By providing the display means on the bottom face side of the tube body, even in a case where the RFID reader/writer is moved, a cell on which processing is performed can be visually checked by performing display with the display means.

In order to achieve the above object, an RFID sample management method related to the invention comprises a first writing step of writing at least any one of information of a cell to be fractionated or arrangement information of a tube body disposed on a well plate, in the RFID tag of the PCR tube described above; a step of fractionating the cell in the PCR tube disposed on the well plate; a step of imaging the fractionated cell and acquiring a cell image; a step of sorting a target cell on the basis of the cell image; a step of reading the information from the RFID tag of the PCR tube with an RFID reader/writer disposed on a side opposite the bottom face of the tube body; and a second writing step of writing information of the target cell in the RFID tag of the PCR tube.

According to the RFID sample management method of the invention, the RFID tag is disposed at the collar part of the tube body, or the lid part, by using the PCR tube described above. Therefore, even in a case where the PCR processing is performed, the information can be managed without breaking the recording of the RFID tag. Additionally, in a case where the information is read from the RFID tag by the RFID reader/writer or also in a case where the information is written in the RFID tag, the RFID reader/writer is disposed on the side opposite to the bottom face of the tube body of the PCR tube, the distance between the RFID tag and the RFID reader/writer can be shortened, and the size of the RFID tag can be made small. In this way, according to the RFID sample management method of the invention, the RFID tag is made small even in a case where the RFID tag is used for the PCR tube. Accordingly, the RFID tag can be installed at the position where a temperature is not applied by the PCR processing. Thus, the RFID tag can be can installed in the PCR tube, and from the step of fractionating the cell, in the step of imaging the fractionated cell and the step of sorting the target cell, and also in the subsequent processing, the cell (sample) can be managed by the RFID tag.

In one aspect of the RFID sample management method related to the invention, it is preferable that the method further comprises a code printing step of describing a code configured in one dimension or two dimensions in the tube body before the step of fractionating the cell.

According to this aspect, the code configured in one dimension or two dimensions is described in the tube body. Accordingly, the information can be individually read by a code reader. Additionally, in a case where the information cannot be read due to a failure of the RFID tag, the information is read from the code configured in one dimension or two dimensions. Accordingly, the sample can be managed.

Here, as preferable one-dimensional codes, for example, CODE 39, NW7, and CODE 128 can be used, and as preferable two-dimensional codes, for example, a quick response (QR) code (Registered Trademark), DataMatrixCode, VeriCode, an RFD417 code, and a CODE49 code can be used. Moreover, it is more preferable to use DataMatrixCode.

In one aspect of the RFID sample management method related to the invention, it is preferable that the method further comprises a character printing step of describing at least any one of the information of the cell or the arrangement information of the tube body on the well plate, in the tube body, before the step of fractionating the cell.

According to this aspect, the information of the cell or the arrangement information of the tube body on the well plate is described. Accordingly, the sample within the PCR tube can be visually checked, without performing the reading with a reader.

In one aspect of the RFID sample management method related to the invention, it is preferable that a display means is provided at a position that faces each tube body, and the method further comprises a step of turning on the display means corresponding to the tube body to which the target cell sorted in the sorting step is fractionated.

According to this aspect, the display means corresponding to the tube body to which the target cell sorted in the sorting step is fractionated is turned on. Accordingly, after the PCR reader/writer is moved, the PCR tube including the target cell can be can be visually checked. Hence, the PCR tube having the cell to be processed can be taken out from the well plate without erroneous reading.

According to the PCR tube of the invention, the RFID tag in which the passive antenna having the directivity in the direction opposite to the bottom face of the tube body, that is, upward directivity, is built is provided at the collar part of the PCR tube, or the lid part. Accordingly, reading can be made from above the PCR tube by the reader/writer. By disposing the RFID tag the collar part of the PCR tube, or the lid part, a temperature can be effectively applied to the PCR tube in the case of the PCR processing. Additionally, by performing reading from above the RFID tag with the reader/writer, the distance between the RFID tag and the reader/writer can be shortened. Thus, the RFID tag can be made small. Hence, also in a small-sized PCR tube, information management can be reliably performed using the RFID tag.

Additionally, according to the RFID sample management system and the RFID sample management method of the invention, the information is recorded on the RFID tag. Accordingly, even in the subsequent step, a sample within a PCR tube can be managed.

DESCRIPTION OF THE PREFERRED EMBODIMENTS

Hereinafter, a PCR tube related to the invention, and an RFID sample management system and an RFID sample management method using this PCR tube will be described with reference to the accompanying drawings. In addition, in the present specification, "to" is used in the meaning including numerical values described before and after "to" as lower limits and upper limits.

<<PCR Tube>>

Figure 1:
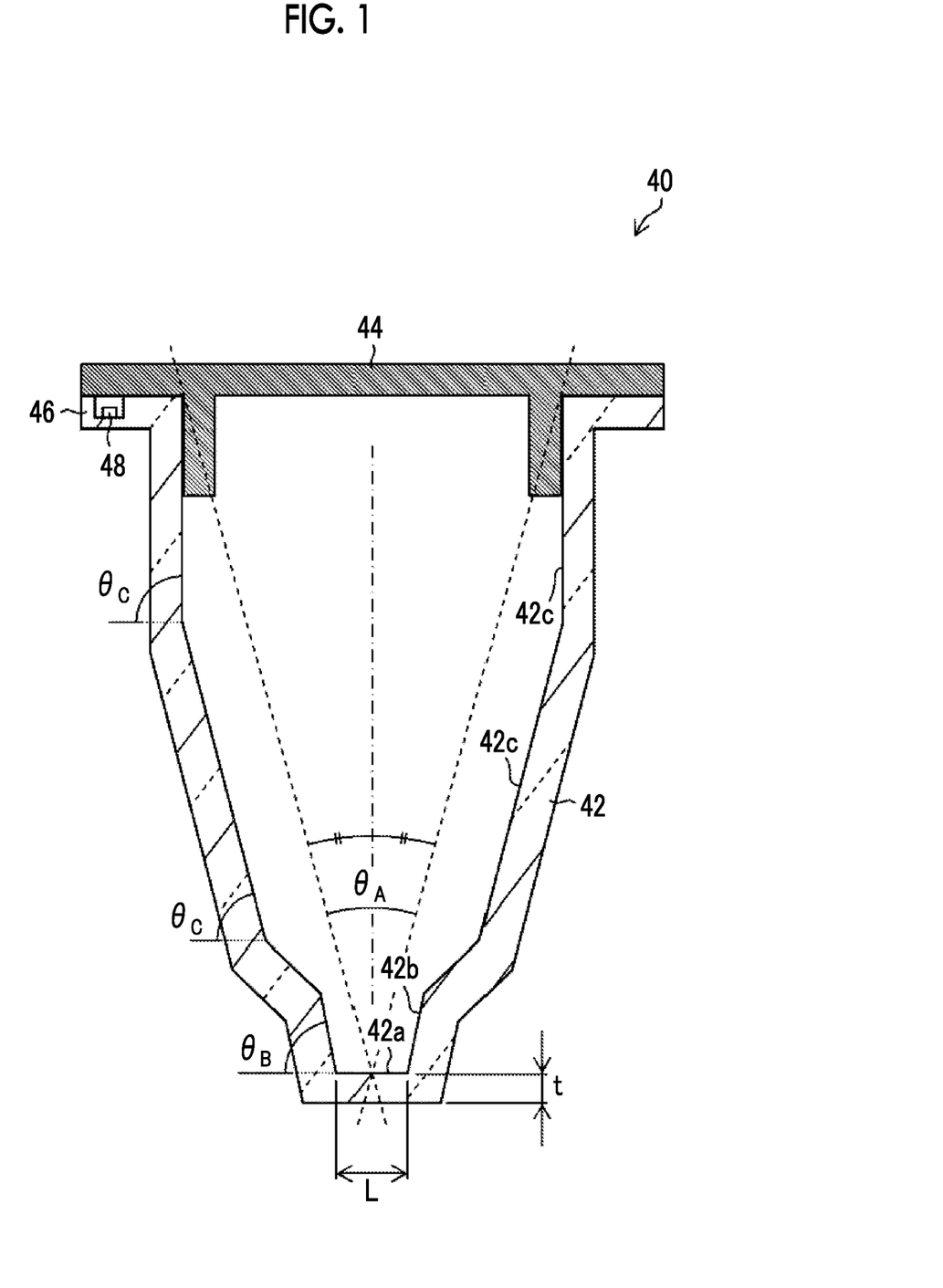
FIG. 1 is a cross-sectional view illustrating the shape of a PCR tube.
Figure 2:
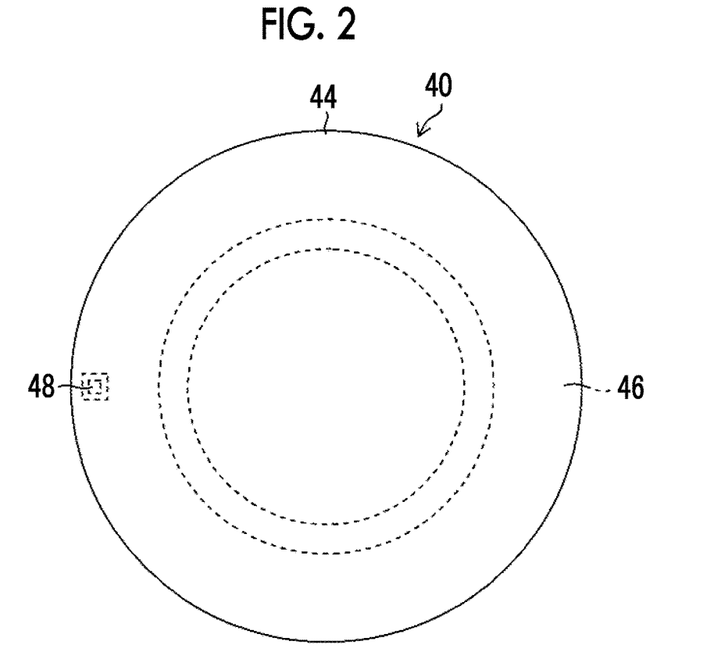
FIG. 2 is a plan view of the PCR tube.

FIG. 1 is a cross-sectional view illustrating an example of the shape of a PCR tube 40 used in the present embodiment, and FIG. 2 is a plan view of the PCR tube 40. The PCR tube 40 illustrated in FIG. 1 is a PCR tube that can be used for imaging of a cell fractionated in the PCR tube 40, using an analysis device 10 illustrated in FIG. 4 to be described below and also for a device that acquires optical information from the cell.

The PCR tube 40 includes a tube body 42, and a lid part 44 on which the tube body 42 is attachably and detachably mounted. The tube body 42 has an opening at one end, and has a collar part 46 around this opening. Additionally, the lid part 44 seals the opening of the tube body 42 in a case where the tube body 42 is mounted. An RFID tag 48 is disposed in the collar part 46, and a sample (cell) within the PCR tube 40 is managed by the RFID tag 48. In addition, the collar part can also be referred to as a flange part.

It is preferable that information of the cell within the PCR tube 40, positional information of a well plate, and the like are stored in the RFID tag 48. By storing the information of the cell and the positional information of the well plate, information can be managed also in a case where the PCR tube 40 is moved from the well plate 19.

The RFID tag 48 is constituted of an IC chip and an antenna. In the present embodiment, the antenna built in the RFID tag 48 is a passive antenna, and has directivity in a direction opposite to a bottom face 42a of the tube body 42, that is, upward directivity in FIG. 1. By making the directivity of the antenna built in the RFID tag 48 upward, an RFID reader/writer disposed in a case where information is written in the RFID tag or information is read can be disposed close to an upper side of the PCR tube 40. Since the antenna built in the RFID tag can be downsized by disposing the RFID tag 48 and the RFID reader/writer close to each other, the RFID tag 48 itself can be downsized.

By downsizing the RFID tag 48, the RFID tag 48 can be installed also in a small container like the PCR tube 40. Additionally, in the PCR tube 40, it is necessary to apply a temperature in order to PCR-process the cell within the PCR tube 40. Hence, in a case where the RFID tag is disposed on a side face or a bottom face of the tube body, there is a case where heat may be applied the PCR processing, the RFID tag may be broken, and information may not be readable. By downsizing the RFID tag 48, since the RFID tag 48 can be installed in the collar part 46, the RFID tag 48 can reliably perform the management of the cell. The RFID tag 48 can be installed in the collar part 46 of the tube body 42 by an embedding method. The size of the RFID tag 48 can be a size of 1 mm×1 mm×0.15 mm (thickness).

Figure 3:
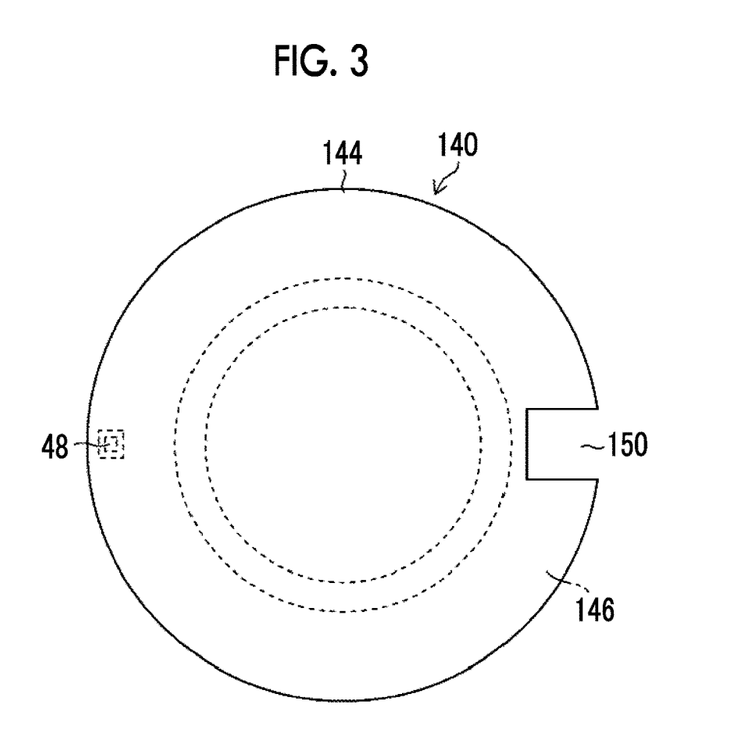
FIG. 3 is a plan view illustrating a modification example of the PCR tube.

FIG. 3 is a plan view illustrating a modification example of a PCR tube 140 having the RFID tag 48 in the collar part. The PCR tube 140 illustrated in FIG. 3 has a positioning part that determines the position of the RFID tag 48 in a case where the tube body is disposed on the well plate.

As the positioning part, a collar part 146 of the tube body and a lid part 144 can be provided with a notch part 150. By disposing the PCR tube such that the notch part 150 is fitted to a protrusion (not illustrated) provided on each well holder 18, the position of the RFID tag 48 of each PCR tube on the well holder 18 can be the same position. As described above, in the present embodiment, the RFID reader/writer is brought close to the upper side of the PCR tube, so that the antenna of the RFID tag 48 can be downsized and the RFID tag 48 itself can be downsized. Hence, in a case where information is read from the RFID tag 48 by the RFID reader/writer, it is necessary to bright the RFID reader/writer close to the RFID tag 48.

In a case where the PCR tube is not provided with the positioning part, it is conceivable that an antenna part of the RFID reader/writer and an antenna part of the RFID tag are separated from each other by the distance of the outer shape of the PCR tube. In this case, in a case where the pitch of the well holders 18 is short, there is a possibility that an RFID tag of a PCR tube next to the RFID tag of the above PCR tube to be originally read may be read. Accurate management of the sample cannot be performed in a case where the RFID tag of the next PCR tube is read. Hence, by making the position of the RFID tag in each PCR tube the same by the positioning part, the antenna of the RFID reader/writer can be disposed at an upper part of the antenna of the RFID tag of each PCR tube. Accordingly, the RFID reader/writer can be prevented from erroneously reading information of a different RFID tag.

Additionally, it is preferable that at least any one of a QR code or a data matrix code is described in a PCR tube body of the PCR tube. The RFID tag simultaneously reads a plurality of PCR tubes with the reader/writer, as will be described below. By describing the QR code and/or the data matrix code in the PCR tube body, the QR code and/or the data matrix code can be individually read, and information can be easily read.

The QR code and/or the data matrix code can be described by printing by an ink jet printer or marking by a laser marker.

Additionally, it is preferable that at least any one of the information of the cell or the arrangement information of the tube body on the well plate is described in the tube body. In order to read the information of the RFID tag, the reader/writer is required, and a code reader is also required in order to read the QR code or the data matrix.

By describing the information of the cell or the arrangement information on the well plate in the tube body, without requiring reading the RFID tag, the QR code or the data matrix code, the information of the PCR tube and the cell within the PCR tube can be checked.

As a method of describing the information of the cell or the arrangement information on the well plate in the tube body, the printing by the ink jet printer or the marking by the laser marker may be performed similarly to a case where the QR code and/or the data matrix code are described. Additionally, the information of the cell or the arrangement information may be described on a seal and pasted.

Referring to FIG. 1, the shape of the tube body 42 will be described. The outer shape of the tube body 42 is a shape in which the tube body is capable of being loaded on a device that performs PCR processing, preferably, a PCR thermal cycler. By making the outer shape correspond to the device that performs the PCR processing, the PCR processing can be performed with the PCR tube, which has been captured an image, as it is. In a case where the tube body is capable of being loaded on the PCR thermal cycler, it is preferable that a gap between the device that performs the PCR processing and the outer shape of the tube body 42 is narrow. By making the gap between the device and the tube body 42 small, a temperature can be efficiently applied to the tube body 42. Additionally, in order to efficiently apply a temperature in a case where the PCR processing is performed, it is preferable that the outer shape and the inner shape of the tube body are substantially the same (analogue), and it is more preferable that the thickness of the side face is uniform from the bottom face to an opening part. By making the thickness uniform, heat is efficiently and uniformly transmitted to the cell within the tube body 42, and a culture solution. Accordingly, it is possible to accurately control the PCR processing.

Figure 4:
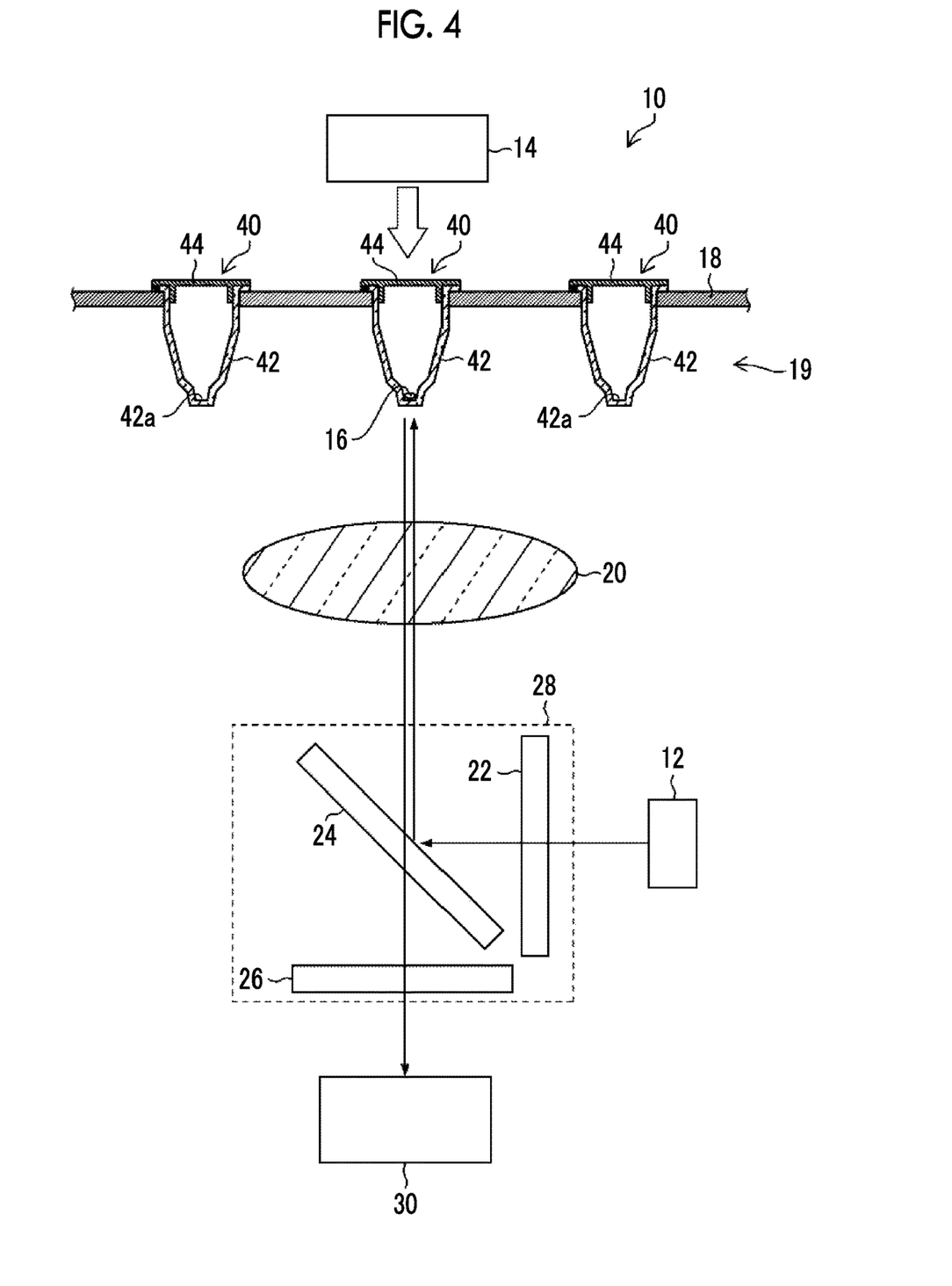
FIG. 4 is a schematic configuration view illustrating the configuration of an analysis device that captures an image of a cell.

In the analysis device 10 illustrated in FIG. 4, excitation light is radiated from the bottom face 42a side of the tube body 42, and fluorescence emission occurs from the cell that has emitted light due to the excitation light transmitted through the tube body 42. In order to receive the fluorescence including the information of the cell, it is required that the material of the tube body 42 is a material that satisfies conditions, such as being transparent, not auto-fluorescing, not scattering the fluorescence, and withstanding a temperature cycle performed by the PCR. Additionally, in order to image the cell 16, it is preferable that the bottom face 42a inside the tube body 42 has a flat shape. By making the bottom face 42a of the tube body 42 flat, it is possible to adjust a focal point to the cell 16, and image analysis of the cell 16 that is present on the bottom face 42a can be accurately performed.

Additionally, it is preferable that side faces 42b and 42c of the tube body 42 are formed in a direction that widens toward the opening part of the container from the bottom face. By making the opening part of the tube body 42 wide, and making the tube body narrow toward the bottom face 42a, the cell 16 can be easily introduced into the tube body 42 and can be easily guided to the bottom face 42a.

In FIG. 1, it is preferable that the side face 42b in contact with the bottom face 42a is formed such that an angle $\theta_B$ on a side face side, which is an angle formed between the bottom face 42a and the side face 42b, is 50° or more and 80° or less. Bubbles in the culture solution can be easily extracted by setting the angle $\theta_B$ formed between the bottom face 42a and the side face 42b to 80° or less. Additionally, by setting the angle $\theta_B$ formed between the bottom face 42a and the side face 42b to 50° or more, a space formed by the bottom face 42a and the side face 42b can be narrowed, and the cell 16 can be dipped in the culture solution with a smaller amount of culture solution. Additionally, the depth of the culture solution within the tube body 42 can be prevented from becomes shallow, and the culture solution and the cell 16 can be prevented from drying out.

As illustrated in FIG. 1, it is preferable that the side face of the tube body 42 are bent in multi-stages. In a case where the side face is bent in multi stages, it is preferable that the side face 42c other than the side face 42b in contact with the bottom face 42a is formed such that an angle $\theta_C$ on the side face side, which is an angle between each side face 42c and a parallel line of the bottom face 42a is 40° or more and 90° or less. In a case where the angle is 40° or more, it is possible to reliably contain the cell on the bottom face without stagnating the cell at an inclination of the side face 42c. Additionally, as the angle is 40° or more, this is preferable because it is possible to narrow the opening of the tube body 42 and it is possible to contain the PCR tube 40 in the narrow space of the well plate 19. Moreover, in a case where the side face is bent in multi stages, it is preferable that the angle $\theta_C$ becomes gradually smaller toward the bottom face 42a from the opening except for the side face 42b in contact with the bottom face 42a. By adopting such a configuration, it is possible to easily guide the cell fractionated in the tube body 42 to the bottom face 42a.

It is preferable that the angle $\theta_A$, which is twice as large as the angle at which a line connecting the center (the center of a circle approximated to a circumscribed circular shape) of the bottom face 42a, and an end part of the opening is formed with respect to a perpendicular straight line to the bottom face, is less than 45°. By setting the angle $\theta_A$ to less than 45 degrees, the opening of the tube body 42 can be prevented from widening, and it is possible to make the space of the well plate 19 small.

Additionally, it is preferable that a thickness t of the bottom face 42a of the tube body 42 is set to 0.2 mm or more and 1 mm or less. As illustrated in FIG. 4, an aspect in which the cell 16 is imaged from the bottom face 42a side of the tube body 42 is preferable. As long as the thickness of the bottom face 42a is less than 1 mm, a lens 20 is allowed to approach the cell 16, which is preferable. Additionally, as long as the thickness is 0.2 mm or more, this is preferable because since a focal point of a scratch or adhering dust or dirt on the outside of the tube body 42 is out of the focal depth and an image to be captured is not affected, only an image of the cell can be captured.

As the material of the tube body 42, in a case where an image is captured, it is preferable to use a material that easily transmits light. Specifically, a material selected from polypropylene, polystyrene, or acrylics can be used. Additionally, the PCR tube using these materials is also excellent in heat resistance, and can perform the PCR processing without degradation of the PCR tube even in a case where the PCR tube is applied to the PCR thermal cycler. In the PCR tube manufactured using these materials, the transmittance thereof with respect to light with a wavelength of 350 nm or more and 800 nm or less is preferably 60% or more, more preferably 70% or more, and still more preferably 80% or more. In addition, in the invention, the "transmittance" is a value (transmittance=transmitted light/incident ray×100) obtained by dividing transmitted light by incident rays. For example, in a case where a beam transmitted in a case where a beam of 100 is made incident is 60, the transmittance is calculated to be 60%. Additionally, as illustrated in FIG. 4, the material of the lid part 44 is also preferably a material that easily transmits light, and is preferably the same material as the tube body 42 in order to radiate the light for measuring the transmitted light of the cell from the lid part 44 side.

In addition, in FIGS. 1 to 3, although the PCR tube that can perform imaging and analysis of the cell fractionated in the PCR tube 40 has been described, the PCR tube of the invention is not limited to this. Cells may be fractionated in other containers and analyzed, a cell to be subjected to the PCR processing may be determined, and then, the cell may be moved to the PCR tube that has the RFID tag at the collar part and can perform the PCR processing.

<<Analysis Device>>

Next, an analysis device to which the PCR tube of the present embodiment is applied and which includes an imaging device for capturing an image will be described. In addition, although a device that analyzes the cell fractionated in the PCR tube will be described as an example of the analysis device, the invention is not limited to this.

FIG. 4 is a schematic configuration view illustrating imaging of a target cell fractionated in the PCR tube, and the configuration of a device that acquires the optical information from the cell. As a preferable aspect, there is an analysis device that allows acquisition of fluorescent emission light from a fluorescent dye labeled on the fractionated cell by the antigen-antibody reaction or the like or acquisition of an light transmission image of the cell resulting from visible light.

The analysis device 10 illustrated in FIG. 4 includes a fluorescence excitation light source device 12 for radiating light for measuring the fluorescence emitted from the target cell; a bright view field light source device 14 that radiates light (visible light) for measuring the transmitted light of the cell; the well plate 19 having PCR tubes 40 each containing the cell 16 serving as a target to be imaged and the well holders 18; a filter group (filter cube) 28 holding the lens 20, an excitation filter 22, a dichroic mirror 24, and a fluorescent filter 26; and an imaging device 30 that images the fluorescence and the transmitted light from the cell 16.

As the fluorescence excitation light source device 12, a high-pressure mercury lamp, a high-pressure xenon lamp, an LED (light emitting diode), a light amplification by stimulated emission of radiation (LASER), or the like can be used. By using these light sources to narrow a wavelength range of the radiation light to be radiated to the cell 16, it is possible to reliably perform high-accuracy analysis. Additionally, as the fluorescence excitation light source device 12, a tungsten lamp, a halogen lamp, a white LED, or the like can be used. Even in a case where these light sources are used, the cell 16 can be irradiated with light with a target wavelength by allowing the excitation filter 22 to transmit only the light with a target wavelength. In addition, the same light source as the bright view field light source device 14 can also be used as the fluorescence excitation light source device 12.

The well plate 19 holds the well holders 18, and the PCR tubes 40 of the present embodiment, and holds the cell 16 serving as an observation target. The cell 16 is supplied to each PCR tube 40 together with a cell culture solution.

The lens 20 magnifies the fluorescence emitted by the cell 16 due to the light output from the fluorescence excitation light source device 12, and the transmitted light obtained by the light output from the bright view field light source device 14 is transmitted through the cell 16. A lens used for optical measurement can be used for the lens 20.

The filter group 28 includes the excitation filter 22, the dichroic mirror 24, and the fluorescent filter 26. As a specific example of such a filter group 28, it is preferable to use a filter cube. For example, Zeiss Filter Set49 (DAPI: 4',6-diamidino-2-phenylindole) can be used. The light radiated from the fluorescence excitation light source device 12 is made to be only the light of the target wavelength range by the excitation filter 22. The light that has transmitted the excitation filter 22 is reflected toward the well plate 19 by the dichroic mirror 24. The fluorescent emission light from the cell 16, which is generated by the excitation light emitted from the fluorescence excitation light source device 12, is captured by the imaging device 30 through the lens 20, the dichroic mirror 24, and the fluorescent filter 26. Since the fluorescence emitted by the excitation light has a wavelength range on a longer wavelength side than the excitation light, it is possible to use the dichroic mirror 24, thereby allowing only the fluorescent emission light to be transmitted therethrough. Moreover, by using the fluorescent filter 26 that allows only the fluorescence to be transmitted therethrough, without transmitting the excitation light, it is possible to perform imaging with information of only the fluorescent emission light from the cell 16 by the imaging device 30. Therefore, the image captured by the imaging device 30 is not affected by the excitation light, and the accuracy of testing by the fluorescent emission light information can be improved.

In the fluorescence imaging caused by the light radiated from the fluorescence excitation light source device 12, immunostaining is normally performed using a plurality of kinds of coloring agents in order to acquire a plurality of pieces of information for one cell in accordance with the test purpose of the cell. In this case, optical information with different wavelengths can be independently acquired by imaging the fluorescence generated from the plurality of kinds of coloring agents of the immunostained cell, using a filter group having transmission characteristics or reflective characteristics suitable for the fluorescence wavelengths of the respective coloring agents. In addition, in a case where the transmitted light of the cell 16 is imaged by the bright view field light source device 14, the imaging is performed in a state where the filter group 28 is detached. Accordingly, the transmitted light can be imaged by the imaging device 30.

The imaging device 30 is not particularly limited as long as to the fluorescence or the transmitted light of the cell 16 fractionated in the PCR tube 40 on the well plate 19 can be imaged. For example, a charge-coupled device (CCD) camera can be used.

As a method of fractionating the cell in the PCR tube, for example, flow cytometry can be performed. Additionally, a plurality of cells can be collectively added dropwise onto a well plate in which PCR tubes and the well plate are integral with each other, and can be fractionated in the PCR tubes in a centrifugal manner (100 rpm·1 minute) or stationary manner. In a case where the PCR tubes and the well plate are formed integrally with each other, it is preferable to provide a cutting introduction mechanism for grooves, cutting lines, printing lines, or the like in a plate. By cutting the plate with this cutting introduction mechanism, it is possible to individually process the PCR tubes.

<<Another Embodiment of PCR Tube>>

Figure 5:
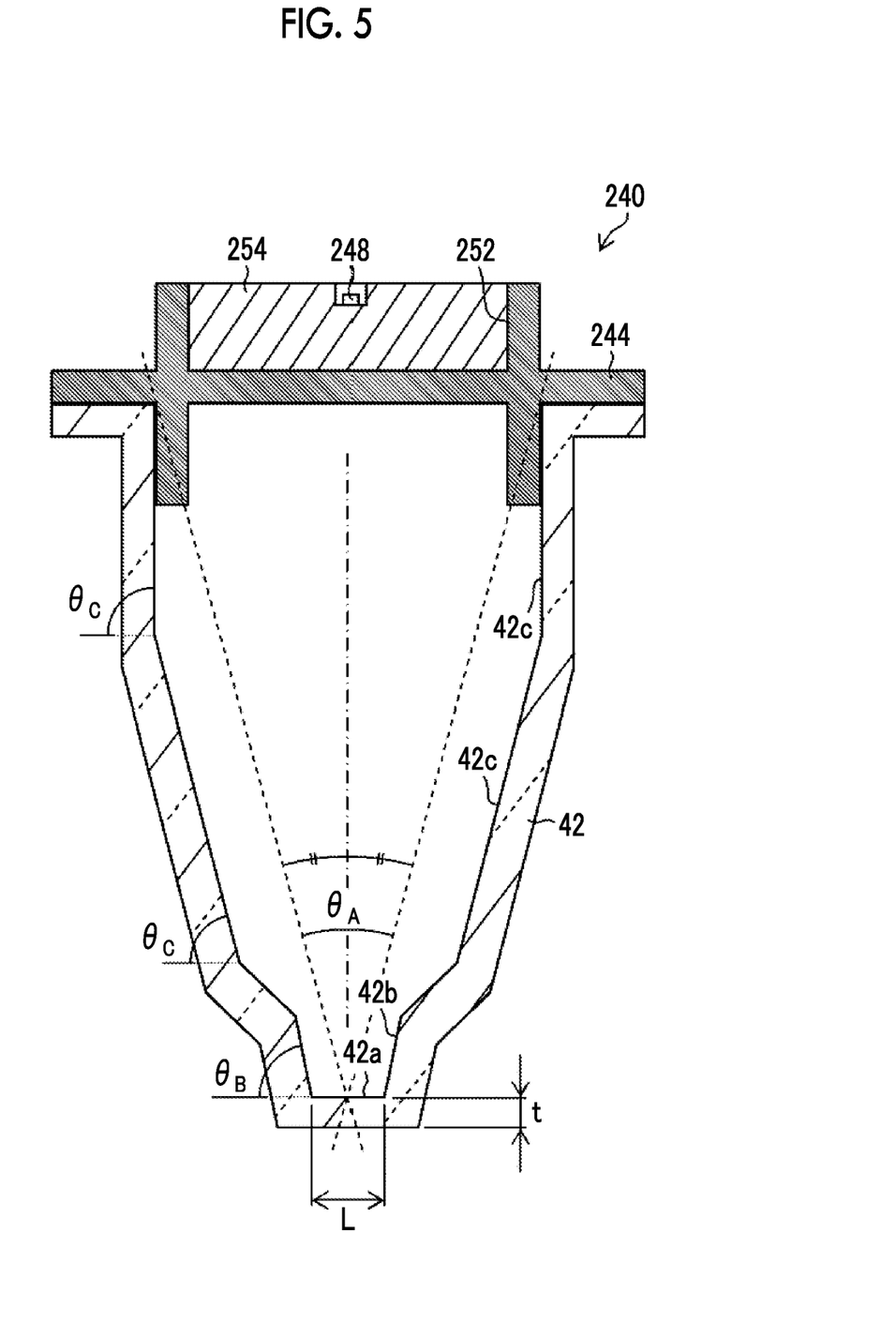
FIG. 5 is a cross-sectional view illustrating the shape of another embodiment of the PCR tube.

FIG. 5 is a cross-sectional view illustrating the shape of another embodiment of the PCR tube. The PCR tube 240 illustrated in FIG. 5 is different from the PCR tube illustrated in FIG. 1 in that an RFID tag 248 is disposed at a lid part 244. By providing the lid part 244 with the RFID tag 248 and making the directivity of an antenna upward, information of the RFID tag 248 can be read by the RFID reader/writer. Additionally, also in the PCR tube 240, the antenna built in the RFID tag 248 can be downsized. Thus, the RFID tag 248 itself can be downsized. Additionally, by providing the lid part 244 with the RFID tag 248, it is possible to prevent a situation in which, due to heating in the PCR processing, the RFID tag breaks and information cannot be read. In addition, since the tube body 42 has the same configuration as the tube body illustrated in FIG. 1 except that the RFID tag is not provided at the collar part, the description thereof will be omitted.

It is preferable that the RFID tag 248 provided in the lid part 244, is attachably and detachably provided in the lid part 244. By making the RFID tag 248 attachable and detachable, the RFID tag 248 can be reused.

In a case where the RFID tag 248 is attachably and detachably disposed, a recess 252 is formed in the lid part 244, a structural body 254 that is attachable in a fitting manner is formed in the recess 252. In a case where the structural body 254 is fitted into the recess 252 of the lid part 244, it is preferable that the RFID tag 248 is disposed within the structural body 254 such that the RFID tag 248 is disposed on an opening side of the recess 252. By providing the RFID tag 248 within the structural body 254 so as to be located on the upper side of the lid part 244, it is possible to perform reading from above the PCR tube 240 with the reader/writer.

It is preferable that a light-transmissive material is used as a material that constitutes the lid part 244 and the structural body 254. In a case where the analysis device illustrated in FIG. 4 is used and in a case where the transmitted light of the cell 16 is measured, light is radiated by the bright view field light source device 14 from the lid part 244 side of the PCR tube 240. Hence, it is preferable that the lid part 244 and the structural body 254 are formed of the light-transmissive material. In addition, in a case where the cell fractionated in the PCR tube is imaged and in a case where it is not determined whether or not the PCR processing is to be performed, the material of the lid part and the structural body is not particularly limited.

In addition, although the RFID tag does not have light transmittance, the size thereof is small, the imaging can be made with the scattered light or the like from the bright view field light source device 14. Therefore, there is no particular problem.

Polypropylene, polystyrene, and acrylic resin can be used as the light-transmissive material. As illustrated in FIG. 5, the RFID tag 248 can be disposed by forming the recess in the structural body 254 made of light-transmissive resin and embedding the RFID tag in the recess with an adhesive.

In a case where the RFID tag 248 is provided in the lid part 244, it is preferable that the RFID tag 248 is provided at the center of the lid part 244. By providing the RFID tag at the center of the lid part 244, even in a case where alignment at the time of being disposed in the well holder 18 is not performed, the position of the RFID tag 248 and the position of the antenna of the RFID reader/writer can be prevented from deviating. However, even in a case where the RFID tag 248 is not provided at the central part of the lid part 244, the distance between the RFID tag and the antenna of the RFID reader/writer is shorter than that in a case where the RFID tag is provided at the collar part. Thus, the RFID tag can be prevented from being erroneously read.

<<RFID Sample Management System>>

Figure 6:
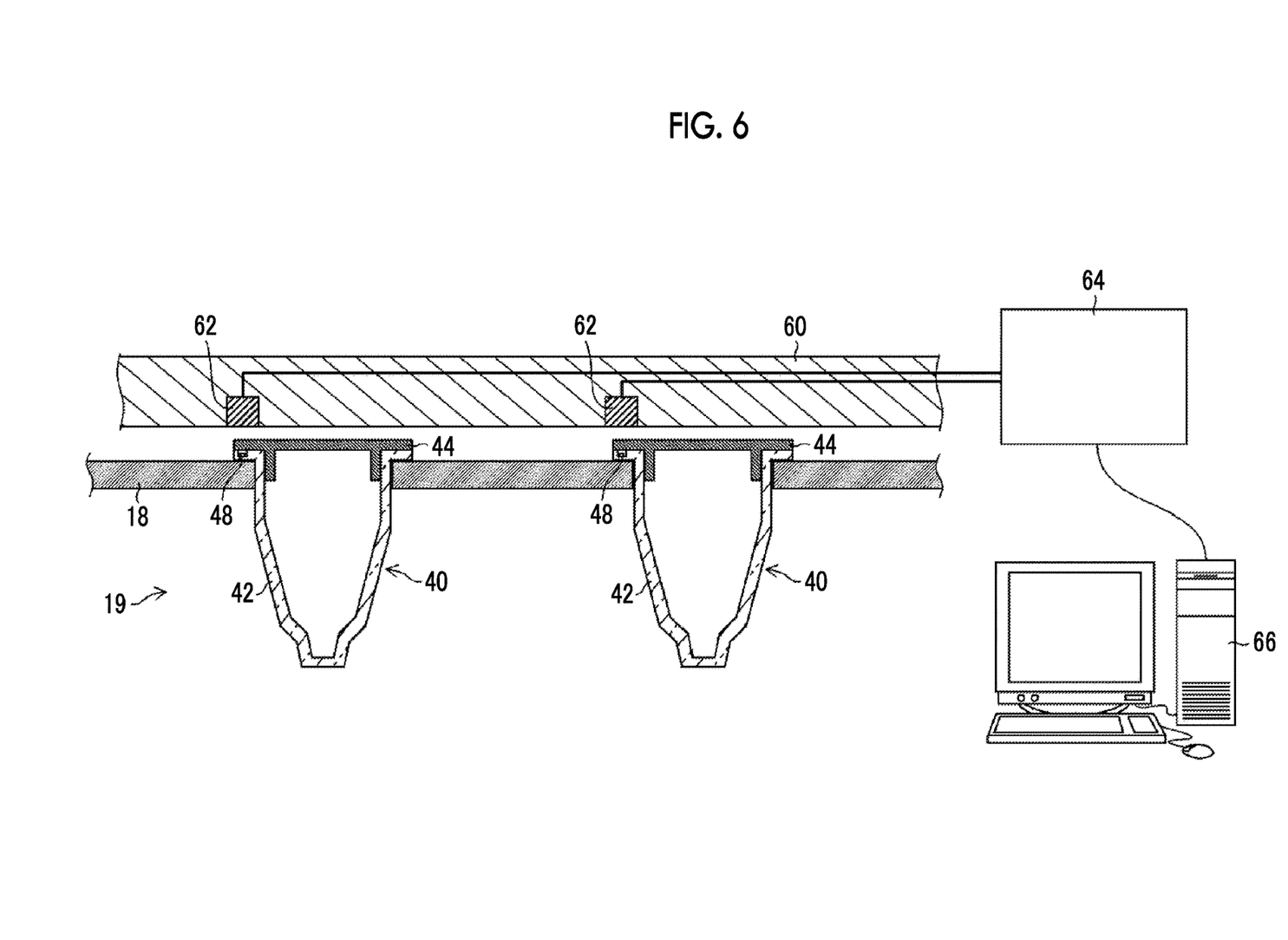
FIG. 6 is a schematic view illustrating an RFID sample management system.

FIG. 6 is a schematic view illustrating an RFID sample management system using the above-described PCR tube. In FIG. 6, although the PCR tube 40 having the RFID tag 48 at the collar part of the tube body 42 has been described, a PCR tube having the RFID tag at the lid part can also be similarly used.

The RFID sample management system includes PCR tubes 40, the well plate 19 having well holders 18 in which the PCR tubes 40 are disposed, and an RFID reader/writer 60 that is capable of being disposed on the lid side of the PCR tubes and has a reader/writer antenna 62. The RFID reader/writer 60 is disposed on the side opposite to the bottom face of the tube body 42, that is, the upper side of the PCR tube 40. In addition, in FIG. 6, although a state where the RFID reader/writer 60 is disposed on the PCR tubes 40 is illustrated, the RFID reader/writer is normally on standby at another location and is disposed in a case where the information of the RFID tags 48 of the PCR tubes 40 is read.

Figure 7A:
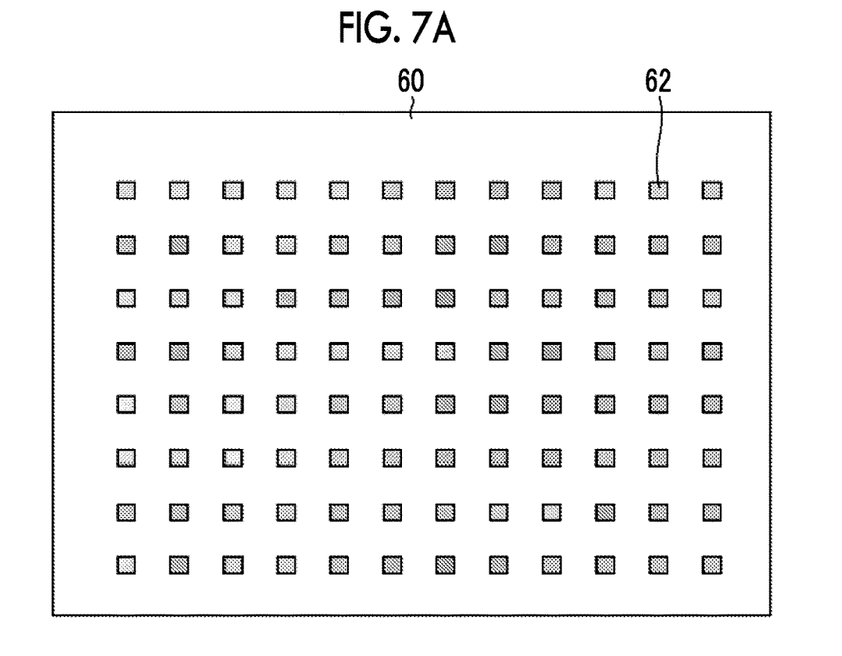
FIG. 7A is a plan view of an RFID reader/writer.
Figure 7B:
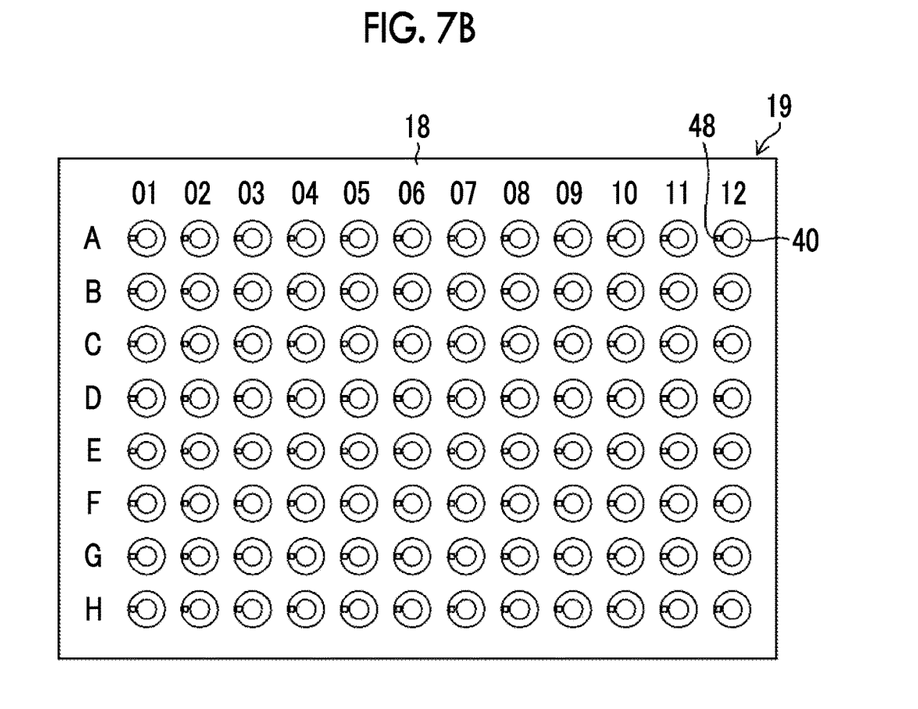
FIG. 7B is a plan view of a well plate in which PCR tubes are disposed.

FIG. 7A is a plan view of the RFID reader/writer 60. FIG. 7B is a plan view of the well plate 19 in which the PCR tubes 40 are disposed. In the well plate 19 illustrated in FIG. 7B, the position (direction) of the RFID tag 48 of each PCR tube 40 is made to the same position (direction) as the RFID tags 48 of the other PCR tubes 40 disposed at the well plate 19 by the positioning part (not illustrated in FIG. 7). The RFID reader/writer 60 has a plurality of reader/writer antennas 62, and the reader/writer antennas 62 are provided at positions corresponding to positions of the well holders (PCR tubes 40) of the well plate 19. As described above, in the RFID tag 48 provided in each PCR tube 40, the RFID tag 48 itself is made small by downsizing its antenna. Thus, the directivity of the antenna is narrow. Hence, the position of each reader/writer antenna 62 is disposed at the position of each well holder, preferably, on the RFID tag 48 of the PCR tube 40.

In a case where positioning the PCR tube 40 is not performed, for example, in a case where the outer shape of the opening of the tube body 42 is 6 mm, the pitch (a shortest distance from one end of a well holder to one end of the adjacent well holder) of the well holders is 9 mm, the RFID tag of a PCR tube disposed at the next well holder may be read in a case where the RFID tag is read by the RFID reader/writer 60. Hence, a corresponding RFID tag can be reliably read by the RFID reader/writer by determining the position thereof by the positioning part.

The information of the cell read by the RFID reader/writer 60 or the arrangement information on the well plate is collated with information of cells or arrangement information on a well plate managed by a computer 66, using a controller 64. Additionally, the information obtained by imaging the cell and the optical information from the cell are again written in the RFID tag 48. Accordingly, the information of the cell within the PCR tube 40 can be managed by the RFID tag 48.

Figure 8:
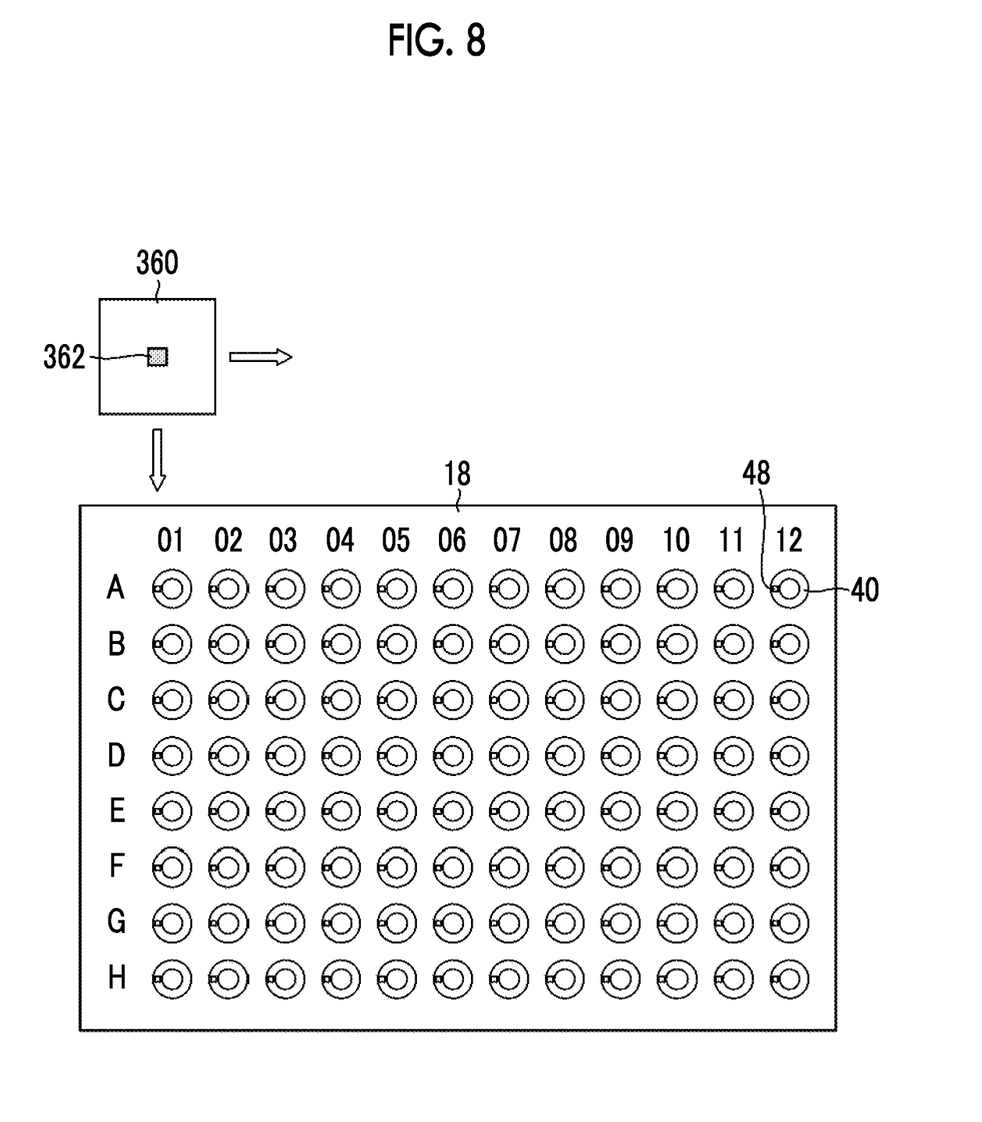
FIG. 8 is a plan view of the well plate in which the PCR tubes are disposed and an RFID reader/writer of another embodiment.

FIG. 8 is a plan view illustrating another aspect of the RFID reader/writer. In an RFID reader/writer 360 illustrated in FIG. 8, one reader/writer antenna 362 is provided, and the information of the RFID tag 48 can be read by scanning the RFID reader/writer 360 with scanning means (not illustrated). In this case, it is not necessary to strictly position each PCR tube 40 strictly as in the case of using the RFID reader/writer illustrated in FIG. 7A. This is because there is no erroneous reading of the RFID tag of the next PCR tube as long as the position can be ascertained.

Figure 9:
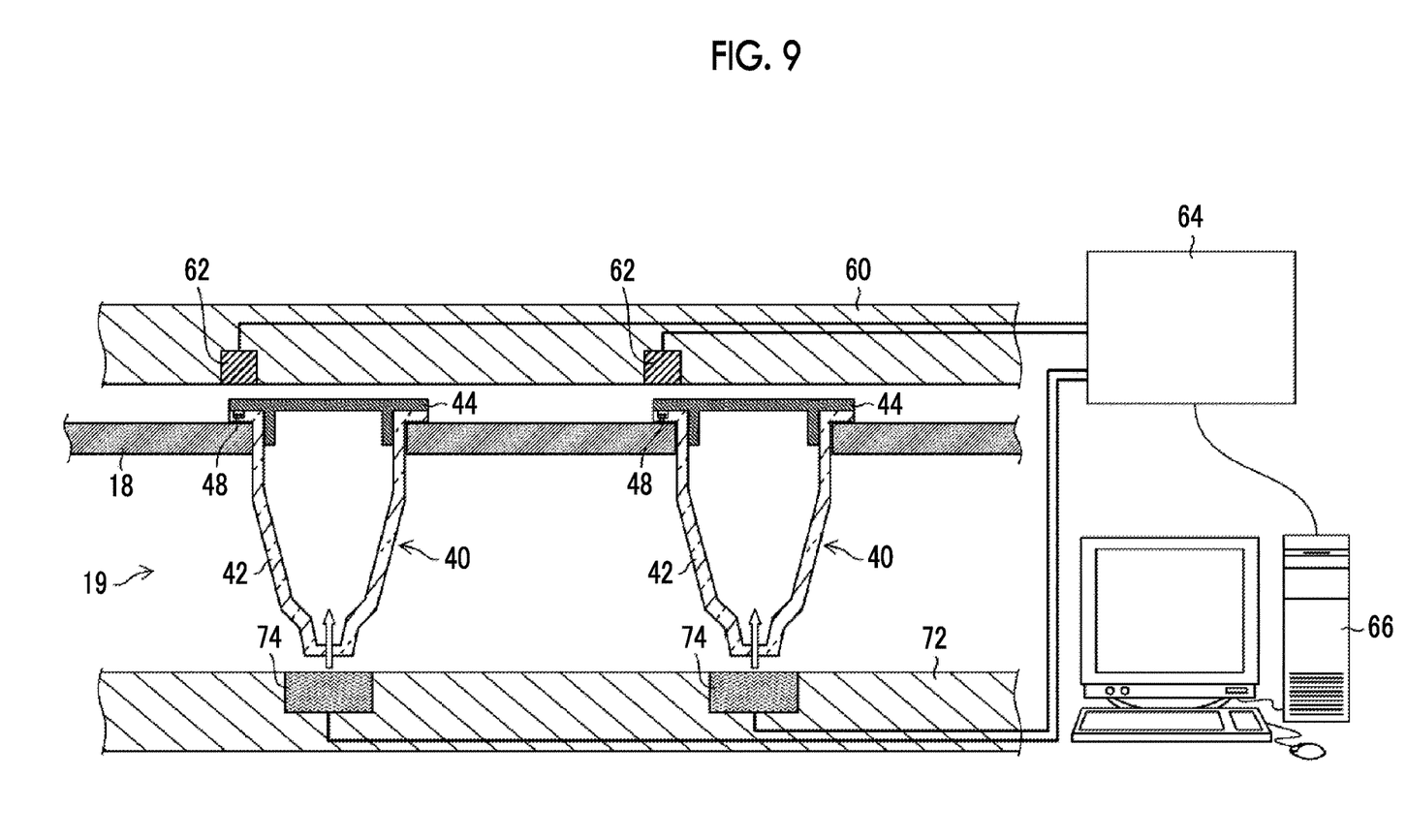
FIG. 9 is a schematic view illustrating another embodiment of the RFID sample management system.

FIG. 9 is a schematic view illustrating an RFID sample management system having display means. As the display means 72, FIG. 9 illustrates an aspect in which an LED display unit 74 is provided at a position facing the bottom face of each PCR tube 40, on the bottom face side of the PCR tube 40.

On the basis of the observation of the cell by the imaging or the optical information of the cell, whether or not the next processing is performed on a cell within a PCR tube is determined in determination means (not illustrated). An LED display unit 74 corresponding to the PCR tube 40 including the cell determined to be subjected to the next processing is turned on by the controller 64. By turning on the LED display unit 74, the cell to be subjected to the next processing can be visually checked. According to the PCR tube 40 of the present embodiment, the RFID reader/writer 60 is disposed above the PCR tube 40 and reads the information of the RFID tag 48. Hence, it is difficult to take out the PCR tube 40 having the cell to be subjected to the next processing while performing the reading with the RFID reader/writer 60. Additionally, in a case where the display means is provided on the RFID reader/writer side, a relevant PCR tube will not be clear anymore by moving the RFID reader/writer.

As illustrated in FIG. 9, by providing the LED display unit 74 on the bottom face side of the PCR tube 40 and turning on the LED display unit 74 at the position corresponding to the PCR tube 40 having the cell that proceeds to the next processing, the relevant PCR tube 40 can be checked even in a case where the RFID reader/writer 60 is moved.

<<RFID Sample Management Method>>

Next, an RFID sample management method using the PCR tube and the RFID sample management system of the present embodiment will be described. The RFID sample management method of the present embodiment includes at least a first writing step of writing information of a cell, arrangement information of a well plate, and the like in an RFID tag of a PCR tube; a step of fractionating the cell in the PCR tube; a step of imaging the fractionated cell and acquiring a cell image; a step of sorting a target cell on the basis of the cell image; a step of reading the information from the RFID tag of the PCR tube with an RFID reader/writer; and a second writing step of writing information of the target cell.

Additionally, prior to the step of fractionating the cell, information may be printed on a tube body. The printing of the information is performed by a code printing step of describing at least any one of a QR code or a data matrix code in the tube body; and a character printing step of describing at least any one of the information of the cell, or the arrangement information of the tube body on the well plate. Additionally, a step of turning on display means corresponding to the tube body to which the target cell sorted by the sorting step is fractionated may be performed.

[First Writing Step]

The first writing step is a step of writing at least any one of the information of the cell fractionated to the RFID tag of the PCR tube or the arrangement information on the well plate in which the PCR tube is disposed. The writing of the information onto the RFID tag can be performed by the RFID reader/writer. Additionally, the same information as the information written in the RFID tag is input to a computer.

[Code Printing Step]

Additionally, the code printing step is a step of describing at least any one of the QR code or the data matrix code in the tube body. By describing the QR code or the data matrix code in the tube body, the information can be individually read by a code reader. The QR code and the data matrix code can be described by printing by an ink jet printer or marking by a laser marker.

[Character Printing Step]

Additionally, the character printing step is a step of describing at least any one of the information of the cell or the arrangement information of the tube body on the well plate in the tube body. By describing the information of the cell or the arrangement information on the well plate in the tube body, the information of the cell within the PCR tube and can be visually checked. The character printing can be performed together with the code printing, or can be performed by the ink jet printer or the laser marker.

[Step of Fractionating Cell]

Additionally, the step of fractionating the cells can be performed by, for example, flow cytometry. Additionally, a plurality of cells can be collectively added dropwise onto a well plate in which PCR tubes and the well plate are integral with each other, and can be fractionated to the PCR tubes in a centrifugal manner or stationary manner.

[Step of Acquiring Cell Image]

The step of acquiring the cell image can be performed using the analysis device illustrated in FIG. 4. The acquisition of the cell image can be performed by acquisition of an light transmission image of the cell by visible light, using a bright view field light source device, acquisition of fluorescent emission light from a fluorescent dye labeled on the cell by an antigen-antibody reaction or the like.

[Step of Sorting Target Cell]

In the step of sorting the target cell, the target cell is sorted on the basis of the cell image obtained by the step of acquiring the cell image. The sorting of the target cell can be performed depending on the shape of the cell, or the shape of a nucleus in the case of a nucleus cell. Additionally, the target cell can be sorted depending on the intensity of the fluorescent emission light.

[Step of Reading Information]

In the step of reading the information, the information is read from the RFID tag of the PCR tube. The reading of the information from the RFID tag is performed using the RFID reader/writer disposed above the RFID tube. By collating the information from the RFID tag with the information managed by the computer (sample management system), the information managed by computer and the information managed by the RFID tag are associated with each other.

[Second Writing Step]

The second writing step is a step of writing the information of the target cell in the RFID tag of the PCR tube. The writing of the information onto the RFID tag can be performed by the RFID reader/writer. Additionally, as the information of the cell, it is preferable to write conditions in the step of fractionating the cell, for example, conditions of the flow cytometry, conditions in the step of sorting the target cell, or the like.

[Step of Turning on Display Means]

The step of turning on the display means is a step of turning on display means corresponding to the tube body to which the target cell sorted in the sorting step is fractionated. By turning on the display means corresponding to the tube body to which the target cell is fractionated, the PCR tube to which the target cell is fractionated can be visually checked.

In this way, according to the RFID sample management method of the present embodiment, the information can be managed with the RFID tag. Thus, sample management can be reliably performed.

EXPLANATION OF REFERENCES

10: analysis device
12: fluorescence excitation light source device
14: bright view field light source device
16: cell
18: well holder
19: well plate
20: lens
22: excitation filter
24: dichroic mirror
26: fluorescent filter
28: filter group (filter cube)
30: imaging device
40, 140, 240: PCR tube
42: tube body
42a: bottom face
42b, 42c: side face
44, 144, 244: lid part
46, 146: collar part
48, 248: RFID tag
60, 360: RFID reader/writer
62, 362: reader/writer antenna
64: controller
66: computer
72: display means
74: LED display unit
150: notch part
252: recess
254: structural body

What is claimed is:

1. A PCR tube comprising:
a tube body that has an opening at one end and has a collar part around the opening; and
a lid part that is attachably and detachably mounted on the tube body and seals the opening of the tube body at the time of mounting,
wherein an RFID tag having a passive antenna built therein is provided at the lid part, and
wherein the antenna has directivity in a direction opposite to a bottom face of the tube body, and the bottom surface of the tube body is on a side opposite to an RFID reader/writer and the lid part.

2. The PCR tube according to claim 1, further comprising:
a positioning part that determines a position of the RFID tag in a case where the tube body is disposed on a well plate.

3. The PCR tube according to claim 2,
wherein the positioning part is a notch part provided in the collar part.

4. The PCR tube according to claim 1,
wherein the RFID tag provided at the lid part is attachable and detachable.

5. The PCR tube according to claim 4,
wherein the RFID tag is disposed within a structural body made of a light-transmissive material, and
wherein the lid part has a recess to which the structural body is attachable in a fitting manner.

6. The PCR tube according to claim 5,
wherein the light-transmissive material is a material selected from polypropylene, polystyrene, and acrylic resin.

7. The PCR tube according to claim 1,
wherein a code configured in one dimension or two dimensions is described in the tube body.

8. The PCR tube according to claim 1,
wherein at least any one of information of a cell or arrangement information of the tube body on a well plate is described in the tube body.

9. An RFID sample management system comprising:
the PCR tube according to claim 1;
a well plate having a well holder in which the PCR tube is disposed; and
the RFID reader/writer that has a reader/writer antenna and is capable of being disposed on a side opposite to the bottom face of the tube body.

10. The RFID sample management system according to claim 9,
wherein a plurality of the reader/writer antennas are provided, and the plurality of reader/writer antennas are disposed at positions corresponding to the well holders of the well plate.

11. The RFID sample management system according to claim 9, further comprising:
scanning means for scanning the RFID reader/writer.

12. The RFID sample management system according to claim 9, further comprising:
determination means for determining whether or not next processing of a cell within the tube body is to be performed; and
display means for displaying the cell determined to be subjected to the next processing by the determination means.

13. The RFID sample management system according to claim 12,
wherein the display means is provided on the bottom face side of the tube body.

14. An RFID sample management method comprising:
a first writing step of writing at least any one of information of a cell to be fractionated or arrangement information of a tube body disposed on a well plate, in the RFID tag of the PCR tube according to claim 1;
a step of fractionating the cell in the PCR tube disposed on the well plate;
a step of imaging the fractionated cell and acquiring a cell image;
a step of sorting a target cell on the basis of the cell image;
a step of reading the information from the RFID tag of the PCR tube with the RFID reader/writer disposed on a side opposite the bottom face of the tube body; and
a second writing step of writing information of the target cell in the RFID tag of the PCR tube.

15. The RFID sample management method according to claim 14, further comprising:
a code printing step of describing a code configured in one dimension or two dimensions in the tube body before the step of fractionating the cell.

16. The RFID sample management method according to claim 14, further comprising:
a character printing step of describing at least any one of the information of the cell or the arrangement information of the tube body on the well plate, in the tube body, before the step of fractionating the cell.

17. The RFID sample management method according to claim 14,
wherein a display means is provided at a position that faces each tube body,
the method further comprising:
a step of turning on the display means corresponding to the tube body to which the target cell sorted in the sorting step is fractionated.

* * * * *